United States Patent
Smithgall

(10) Patent No.: US 7,366,340 B1
(45) Date of Patent: Apr. 29, 2008

(54) METHOD AND SYSTEM FOR OPTICALLY DETERMINING PERPENDICULARITY OF END SURFACE OF PART FORMED FROM PARALLEL CHANNELS

(75) Inventor: Brian Smithgall, Bozeman, MT (US)

(73) Assignee: Reflect Scientific (DBA) Miralogix, Bozeman, MT (US)

( * ) Notice: Subject to any disclaimer, the term of this patent is extended or adjusted under 35 U.S.C. 154(b) by 693 days.

(21) Appl. No.: 10/873,942

(22) Filed: Jun. 22, 2004

(51) Int. Cl.
*G06K 9/00* (2006.01)

(52) U.S. Cl. ............... 382/141; 264/177.12; 264/630; 356/237.6; 428/116; 428/593

(58) Field of Classification Search ............... 382/141, 382/151–152; 55/523, DIG. 30, 466, 282; 428/116, 188, 117, 593; 264/177.12, 630, 264/DIG. 48; 210/510.1; 422/180; 165/165, 165/DIG. 395, 166; 502/527.21, 527.18; 60/311; 52/793.1; 356/237.6

See application file for complete search history.

(56) References Cited

U.S. PATENT DOCUMENTS

| | | | |
|---|---|---|---|
| 6,040,064 A * | 3/2000 | Bruck et al. | 428/593 |
| 6,084,670 A | 7/2000 | Yamazaki et al. | |
| 2001/0028452 A1 | 10/2001 | Yoneda | |
| 2003/0081202 A1 | 5/2003 | Yoneda | |
| 2003/0174320 A1 * | 9/2003 | Yokoyama et al. | 356/237.6 |
| 2004/0013582 A1 * | 1/2004 | Ichikawa et al. | 422/180 |
| 2005/0100486 A1 * | 5/2005 | Ichikawa et al. | 422/180 |

* cited by examiner

*Primary Examiner*—Sheela Chawan
(74) *Attorney, Agent, or Firm*—McKee, Voorhees & Sease, P.L.C.

(57) ABSTRACT

A method and system for inspecting a honeycomb structure having a plurality of parallel channels includes aligning the honeycomb structure with an image sensing device such that the channels of the honeycomb structure are tilted with respect to the parallel channels of the honeycomb structure. An image of the honeycomb structure is then acquired. The image is processed in order to determine the perpendicularity of the end surface of the honeycomb structure.

18 Claims, 2 Drawing Sheets

METHOD AND SYSTEM FOR OPTICALLY DETERMINING PERPENDICULARITY OF END SURFACE OF PART FORMED FROM PARALLEL CHANNELS

BACKGROUND OF THE INVENTION

The present invention relates to inspection of parts. More particularly, the present invention relates to optical inspection of parts that are formed from parallel channels in a honeycomb-like structure. One example of such a part is an automotive catalytic converter part.

Catalytic converters are blocks of parallel tubes or channels made by extrusion. Optical techniques have been used in the past to identify blockages in these tubes. For example, Image Labs International, formerly known as Vision 1, sold the Vision Pluggage Inspection System. Also, U.S. Patent Publication No. 2003/0174320 discloses a piercing inspection apparatus that inspects the piercing of a honeycomb structure.

However, despite these advances, problems remain. In particular, it should be realized that catalytic converters are blocks of parallel tubes or channels made by extrusion. These extrusions are generally cut-off to form the blocks. It is important for the end cut to be perpendicular to the tubes for packaging and airflow reasons. Currently, the inspection of the end cuts of the catalytic converters is a purely mechanical process. Fixtures are used to align the catalytic converters to determine if the ends of the parts are perpendicular with the parallel channels. There is no reliable way to quickly or optically measure the perpendicularity of the end cut relative to the tubes.

Therefore, it is a primary object, feature, or advantage of the present invention to improve upon the state of the art.

It is a further object, feature, or advantage of the present invention to provide a method and system for inspection of structures formed from parallel tubes.

Another object, feature, or advantage of the present invention is to provide a method and system for determining the perpendicularity of an end surface of a series of parallel channels or tubes or the alignment of the group of parallel channels or tubes.

It is a further object, feature, or advantage of the present invention to provide a method and system for optically measuring the perpendicularity of the end cut of a series of parallel channels or tubes.

A still further object, feature, or advantage of the present invention is to provide a method and system for determining the perpendicularity of the end cut of a series of parallel channels or tubes that is reliable.

These and/or other objects, features, or advantages of the present invention will become apparent from the specification and claims that follow.

SUMMARY OF THE INVENTION

The present invention relates to a method and system for inspecting a honeycomb structure. According to one aspect of the present invention, a method is provided for inspecting a honeycomb structure. The honeycomb structure has a plurality of parallel channels. There is a central longitudinal axis extending through the honeycomb structure which is parallel with the plurality of channels. According to the methodology of this aspect of the invention, the honeycomb structure is aligned with an image sensing device such as a camera. The image sensing device is aligned so that a center of a field of view of the image sensing device defines an optical axis and the optical axis is off-axis or tilted with respect to the central longitudinal axis. Next a representation of an image of the honeycomb structure is acquired using the image sensing device. This representation of the image is compared with an ideal representation of a perpendicular cut honeycomb structure to determine the perpendicularity of the end surface of the honeycomb structure relative the channels of the honeycomb structure.

According to another aspect of the present invention, a method for inspecting a part is disclosed. The part is comprised of a plurality of parallel channels extending through the part from a first end surface to a second end surface. The part can be a catalytic converter. The method is used to determine the perpendicularity of the first end surface relative to the axis defined by the parallel channels. According to the method, a light source illuminates the second end surface from behind the part so that light is projected through the parallel channels of the part. The light is then projected to a lens and then to an image sensing device. The image sensing device acquires an image. The image is then processed to determine the perpendicularity of the first end surface of the part.

According to another aspect of the present invention, a system to optically inspect a honeycomb structure having a plurality of parallel channels is disclosed. There is a central longitudinal axis extending through the honeycomb structure parallel with the plurality of parallel channels. The honeycomb structure has a first end surface and an opposite second end surface. There is an image sensing device positioned so that a center of a field of view of the image sensing device defines an optical axis aligned approximately with the honeycomb structure. There is a converging lens positioned between the image sensing device and the first end surface of the honeycomb structure. A backlight is positioned along the optical axis behind the second end surface of the honeycomb structure to illuminate the plurality of parallel channels. A processing system is operatively connected to the image sensing device and is adapted to determine perpendicularity of the first end surface of the honeycomb structure by comparing the representation acquired by the image sensing device with a known representation of an ideal honeycomb structure.

DETAILED DESCRIPTION OF THE PREFERRED EMBODIMENT

The present invention is a method and system for inspecting a part. The type of part of interest is a part that is comprised of a plurality of parallel channels. Such a part can be described as having a honeycomb structure. One specific example of such a part is a catalytic converter. The present invention, however, contemplates that other specific parts having a plurality of parallel channels could be inspected according to the method and system disclosed herein. The type of inspection of interest is a determination of the perpendicularity of an end surface of the part with the parallel channels that comprise the part.

Figure 1:
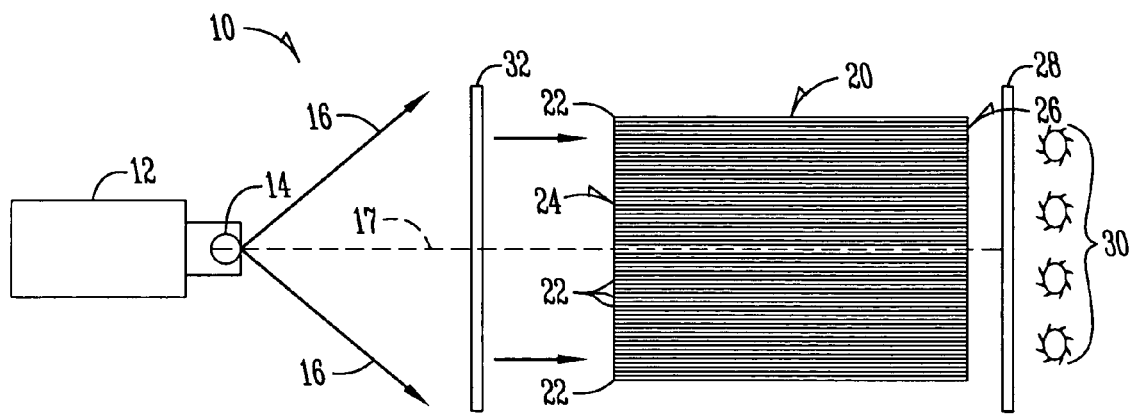
FIG. 1 is a diagram of a prior art system for detecting blockages or pluggage of the channels.

FIG. 1 provides background information showing a prior art system that is used for determining pluggages of the parallel channels of the part. This prior art system has been used for detecting pluggages in catalytic converters. The present invention is directed towards a different type of problem associated with catalytic converters. In particular, the present invention is related to determining the perpendicularity of the end surface relative to the parallel channels.

Figure 2:
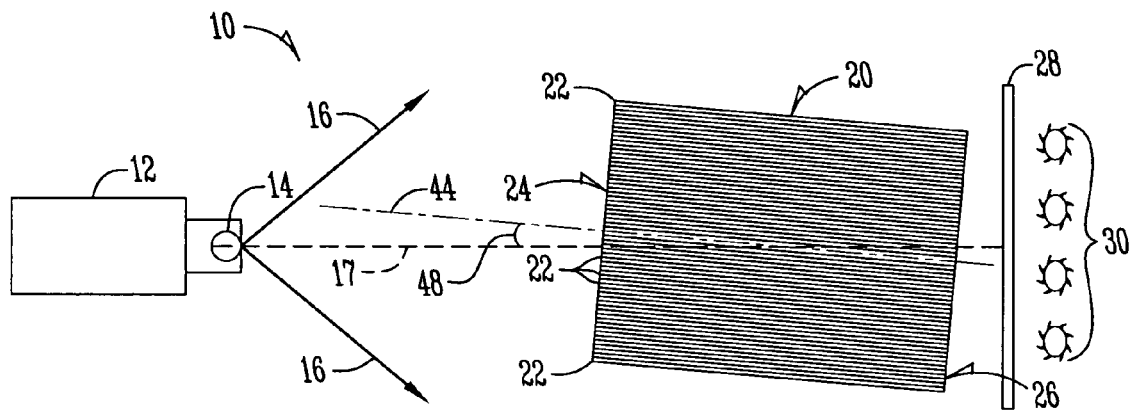
FIG. 2 is one embodiment of an optical system according to the present invention.

FIG. 2 illustrates one embodiment of the present invention. In FIG. 2, a system 10 for detecting perpendicularity is disclosed. In FIG. 2, there is a camera 12 having a lens 14. The lens 14 may be integrated into the camera, but need not be. In addition, the lens 14 may be comprised of a combination of constituent lenses, one of which may be a Fresnel lens. Use of the term "lens" herein means one or more lenses. Note that lines 16 are shown extending outwardly from the lens 14 illustrating the field of the view of the lens. Line 17 is shown to define an optical axis which is centered in the field of view.

A part 20 is also illustrated. The part 20 is comprised of a plurality of channels. The part 20 can also be described as being a honeycomb structure. The particular part 20 shown is a catalytic converter. The part 20 includes a plurality of channels 22. Preferably the channels 22 are narrow. The particular geometric configuration of the channels 22 can vary. For example, the channels can be tubular, rectangular, hexagonal, or of other shapes or configurations.

Part 20 has first end surface 24 and second end surface 26. The end surface 24 and 26 shown are approximately straight cut end surfaces, however the present invention contemplates other geometries. Note that the alignment of the part is off axis or tilted with respect to the optical axis 17 between the camera 12 and a diffuser 28 associated with the backlight 30.

Figure 3:
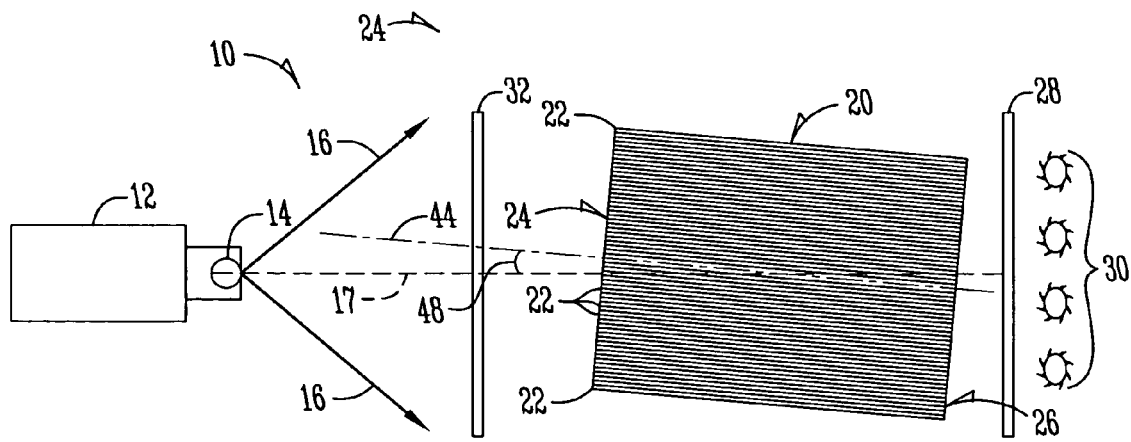
FIG. 3 is another embodiment of an optical system according to the present invention.

FIG. 3 illustrates another embodiment of the system. In FIG. 3, the system 40 includes the same camera 12 with lens 14. Also, the same part 20 is shown with the same diffuser 28 and backlight 30. In the embodiment of FIG. 3, however, an optional lens 32 which may be a converging lens such as a Fresnel lens is also shown. Also shown in FIG. 3 is the optical axis 17 that runs between the camera 12 and the backlight 30. Note that the optical axis 17 is at an angle 48 with a longitudinal axis 44 of the part 20. In other words, the part 20 is tilted with respect to the optical axis 17.

One should appreciate that the lens 32 is optional. The present invention contemplates that any lens used may be a combination of several lenses, one of which may be a Fresnel lens. The present invention contemplates that all lenses used may be integrated into the lens of the camera. As shown in FIG. 3, the result of viewing the block with a tilt and a lens system that does not look straight through the tubes is that there is a small bright spot in the field of view in the direction that the tubes line up. The displacement of the bright spot from the center of the field of view of the camera represents the shift. The formula for the relationship is:

$$\theta = \arctan(\text{shift in pixels} \times \text{pixel size}/\text{working distance})$$

The resulting image acquired and placement of the bright spot within the image can be used to determine the perpendicularity of the end surface of the part. It is further noted that the system can also be used to detect that the tubes 22 are not actually parallel.

As shown in FIG. 3, the converging lenses may consist of a lens on a camera and a second lens (for example a Fresnel) or, as in FIG. 2, just a lens on the camera. A pair of lenses may be combined and treated as a single lens. The lens is arranged so that rays on each side converge, that is that the lens is focused at a point beyond the back surface of the array of channels. Also, as shown in FIGS. 2 and 3, the system should have lighting behind the part. Also, the lens convergence angle determines the relative movement of the hot spot according to the angle change, and thus the accuracy. It also determines the variations of angles that can be measured.

Figure 4:
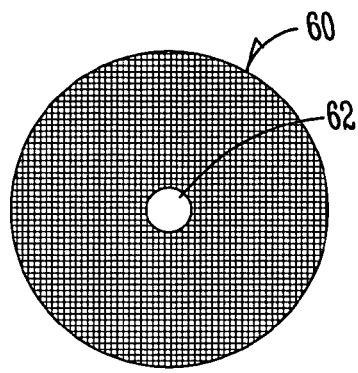
FIG. 4 is an illustration of an image with a bright spot.

FIG. 4 illustrates a representation of an image showing a surface of the catalytic converter 60 with a hot spot or bright spot 62. The position of the bright spot 62 is based in part on the perpendicularity of the end surface 48.

Figure 5:
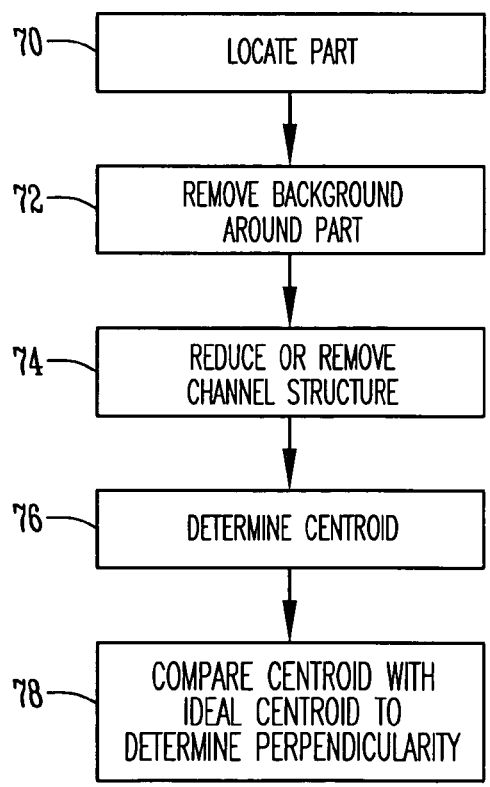
FIG. 5 is a flow chart showing one of the methods of image processing according to the present invention.

Thus, the present invention provides for determining the orientation of tubes as presented. The present invention contemplates determining the offset or the perpendicularity of the first end surface of the part. The perpendicularity can be determined according to the methodology of FIG. 5. As shown in FIG. 5, first the part within an image is located in step 70. The present invention contemplates that any of numerous well known image processing algorithms can be used. Next in step 72, background around the part is removed by making the background dark.

Then, in step 74 the channel structure of the part is removed. This can be performed by smoothing or dilating the image to reduce and remove the channel structure. Then in step 76, the centroid of the bright spot in the middle of the part is determined. Then in step 78 the centroid is compared with an ideal centroid to determine the amount of perpendicularity.

The present invention contemplates instead of using an ideal object to create an ideal centroid, an ideal centroid can be determined by taking a part and capturing images of the part rotated in 90° steps. Therefore, there would be four orientations of the part. The bright spot location for each orientation can then be computed. These locations can then be averaged in order to determine the ideal center.

The present invention contemplates numerous variations in the particular structure used, steps performed, types of parts, and other variations. These and other variations are within the spirit and scope of the invention.

What is claimed is:

1. A method for inspecting a honeycomb structure having a plurality of parallel channels, a central longitudinal axis extending through the honeycomb structure and parallel with the plurality of channels, comprising:
    aligning the honeycomb structure with an image sensing device such that a center of a field of view of the image sensing device defines an optical axis and the optical axis is approximately aligned with the honeycomb structure;
    acquiring a representation of an image of the honeycomb structure using the image sensing device;
    comparing the representation of the image with an ideal representation of a perpendicularly cut honeycomb structure to determine perpendicularity of the channels of the honeycomb structure to an end surface of the honeycomb structure, wherein the comparing includes image processing to determine a centroid position of a bright spot within the image of the honeycomb structure and comparing the centroid position to an ideal centroid position.

2. The method of claim 1 wherein a converging lens is positioned along the optical axis between the image sensing device and the honeycomb structure.

3. The method of claim 1 wherein the image sensing device is a camera.

4. The method of claim 3 wherein the camera includes a lens.

5. The method of claim 2 wherein the converging lens is a Fresnel lens.

6. The method of claim 1 further comprising providing a backlight such that the honeycomb structure is positioned between the backlight and the image sensing device.

7. The method of claim 1 wherein the honeycomb structure is a catalytic converter.

8. The method of claim 1 wherein the ideal centroid position is determined by taking a honeycomb structure, capturing images of the honeycomb structure rotated in 90° steps and computing locations of the bright spot and averaging the locations to determine the ideal centroid position.

9. The method of claim 1 wherein the central longitudinal axis of the part is tilted relative to the optical axis.

10. A method of inspecting a part, the part comprised of a plurality of parallel channels extending through the part from a first end surface to a second end surface, the method for determining perpendicularity of the first end surface to a longitudinal axis of the part, the method comprising:
    illuminating a light source behind the second end surface such that light is projected through the parallel channels of the part;
    receiving the light at an image sensing device and acquiring an image;
    determining a centroid position of a bright spot within the image;
    comparing the centroid position to an ideal centroid position to determine the perpendicularity of the first end surface of the part.

11. The method of claim 10 wherein the part is a catalytic converter.

12. A system to optically inspect a honeycomb structure having a plurality of parallel channels, a central longitudinal axis extending through the honeycomb structure parallel with the plurality of parallel channels from a first end surface to a second end surface, comprising:
    an image sensing device positioned such that a center of a field of view of the image sensing device axis defines an optical axis;
    a converging lens positioned between the image sensing device and the first end surface of the honeycomb structure;
    a backlight positioned along the optical axis behind the second end surface of the honeycomb structure to illuminate the plurality of parallel channels;
    a processing device system operatively connected to the image sensing device adapted to determine perpendicularity of the first end surface of the honeycomb structure by comparing the representation acquired by the image sensing device with a known representation of an ideal honeycomb structure.

13. The system of claim 12 wherein the image sensing device is a camera and the converging lens is integrated into the camera.

14. The system of claim 13 further comprising a second lens between the camera and the honeycomb structure.

15. The system of claim 12 wherein the honeycomb structure is a catalytic converter.

16. The system of claim 12 wherein the central longitudinal axis of the part is tilted relative to the optical axis.

17. The system of claim 12 wherein the comparing includes image processing to determine a centroid position of a bright spot within the representation and comparing the centroid position to an ideal centroid position.

18. A method for inspecting a honeycomb structure having a plurality of parallel channels, a central longitudinal axis extending through the honeycomb structure and parallel with the plurality of channels, comprising:
    aligning the honeycomb structure with an image sensing device such that a center of a field of view of the image sensing device defines an optical axis and the optical axis is approximately aligned with the honeycomb structure;
    acquiring a representation of an image of the honeycomb structure using the image sensing device;
    determining perpendicularity of the channels of the honeycomb structure to an end surface of the honeycomb structure using image processing to compare the representation of the image with an ideal representation of a perpendicular cut honeycomb structure.

* * * * *